United States Patent [19]

Jones et al.

[11] 4,421,544

[45] Dec. 20, 1983

[54] LEGUME-INOCULATING COMPOSITION

[75] Inventors: James L. Jones, Columbus; E. Glen Keyser, Grove City; James C. Phillips, Plain City, all of Ohio

[73] Assignee: Agrigenetics Corporation, Columbus, Ohio

[21] Appl. No.: 383,586

[22] Filed: Jun. 1, 1982

[51] Int. Cl.³ ............................................. C05F 11/08
[52] U.S. Cl. ........................................... 71/7; 435/42; 435/253; 435/254
[58] Field of Search ................. 435/42, 168, 243, 253, 435/254; 71/6, 7

[56] References Cited

U.S. PATENT DOCUMENTS 3,013,946  12/1961  Lumb et al. .................... 435/254 X

FOREIGN PATENT DOCUMENTS 571467  9/1977  U.S.S.R. ............................... 435/42

*Primary Examiner*—Ferris H. Lander
*Attorney, Agent, or Firm*—William S. Rambo

[57] ABSTRACT

A viable fungal culture of the genus Arthrobotrys is combined with substantially dormant Rhizobia bacteria and a carbohydrate nutrient to provide a legume-inoculating composition which may be packaged, transported and stored for a reasonable time prior to its usage.

6 Claims, No Drawings

LEGUME-INOCULATING COMPOSITION

BACKGROUND OF THE INVENTION

This invention deals generally with agrobiological compositions and more particularly to an improved legume-inoculating composition which contains an essential ingredients an Arthrobotrys fungus, a Rhizobium bacterium and a nutrient for sustaining the fungus and bacterium for a period of time following introduction of the composition into the soil. The use of various species of dormant and/or growing Rhizobia bacteria for the preplant, or in-the-soil, inoculation of legume seeds is well and familiarly known as evidenced by the disclosure of U.S. Pat. No. 3,168,796 issued Feb. 9, 1965 to James R. Scott et al. So, also, the use of various species of fungi to control plant parasitic nematodes has also been proposed by various authors. See, for example, articles entitled: "Nemin and The Nematode-Trapping Fungi" by Pramer and Kuyama, *Bacterial. Rev.* vol. 27 (1963) pp. 282-292 and "Interaction Between Nematophagous Fungi And Plant-Parasitic Nematodes: Attraction, Induction Of Trap Formation And Capture" by Jansson and Nordbring-Hertz, *Nematologica* 26 (1980): pp. 383-389.

However, so far as we are aware, there has been no prior disclosure or use of a stable, agrobiological product of commerce which combines a viable fungus, with a substantially dormant bacterium and a growth-promoting nutrient for said fungus and bacterium.

SUMMARY AND OBJECTS OF THE INVENTION

The present invention provides an improved legume-inoculating composition which contains, as essential ingredients: a viable Arthrobotrys fungus (preferably *Arthrobotrys amerospora*), a species of Rhizobium bacterium specific to the legume to be inoculated and a carbohydrate nutrient for said fungus and bacterium selected from the class consisting of a monosaccharide, a disaccharide, a polysaccharide, glycerol and cornmeal. The fungus, bacterium and nutrient are present in the following minimal amounts per gram of the composition:

fungus—at least one viable propagule,
bacterium—at least $1 \times 10^6$ cells or CFU (colony forming units),
nutrient—at least 0.001 g.

The composition of this invention may be packaged and marketed in the forms of a frozen liquid concentrate, a dry preplant seed-coating powder, or in the form of a granular material for direct incorporation into the soil or seed furrow.

The principal object of this invention is to provide an improved legume-inoculating composition which not only stimulates root nodule formation with improved nitrogen fixation, but also produces healthier plants with reduced nematode infections and materially increased crop yields. A further object is to provide a stable legume-inoculating composition which may be packaged, transported and stored either as a frozen liquid concentrate, a dry powder, or a granular bulk material for a reasonable time prior to its in-soil usage.

Additional and further objects and advantages of this invention will become more readily apparent by reference to the following description.

DESCRIPTION OF PREFERRED EMBODIMENTS

According to this invention, an improved legume-inoculating composition is prepared by combining a fungal culture of the genus Arthrobotrys with a bacterial culture of the genus Rhizobium and one or more carbohydrate nutrients for the fungi and bacteria.

The species of Arthrobotrys fungus may be selected from the class consisting of *A. amerospora* (ATCC 34468), *A. conoides* (ATCC 15594), *A. oligospora*, (ATCC 16234) and *A. musiformis* (ATCC 15596), but *A. amerospora* is preferred because of its comparatively faster growth rate and its diverse nematode control capabilities.

The species of Rhizobium bacterium specific to the species of legume to be inoculated is selected as the second essential ingredient of the present composition. Thus, *Rhizobium japonicum* is selected when soybeans are to be inoculated. Rhizobium "cowpea miscellany" when peanuts are to be inoculated, *Rhizobium phaseolus* for green beans, *Rhizobium melilotus* for alfalfa, *Rhizobium leguminosarum* for garden peas, *Rhizobium trifolium* for clovers, etc.

The carbohydrate nutrient may be selected from the class consisting of monosaccharides, disaccharides, polysaccharides, glycerol and cornmeal or mixtures thereof.

The present legume-inoculating compositions may also include trace quantities of various inorganic minerals known to stimulate plant growth, such as for example: sodium molybdate, ferrous sulphate, potassium phosphates, borax, etc.

Dry, powdered and granular forms of the present compositions may also include various inert fillers or carriers, such as montmorilonite and sodium bentonite clays, ground corncobs, ground peat, etc.

The fungi and bacteria utilized in the present legume-inoculating compositions may be grown in accordance with standard procedures which are well known in the art. As a specific example, a strain of *Arthrobotrys amerospora* maintained on cornmeal agar was obtained from the American Type Culture Collection (ATCC). The Arthrobotrys fungus was transferred from the cornmeal agar to 60 ml. of an aqueous yeast-glucose growth media made up of 1 part (by weight) yeast extract, 1 part glucose (Cerelose hydrate) and 100 parts water and was maintained in the yeast-glucose media at a temperature between 24°-30° C. for a period of three days. This mass was then transferred into a 2800 ml. Fernbach flask containing 1500 ml. of a cornmeal broth prepared by suspending 1 part (by weight) of cornmeal in 80 parts of water. The culture was maintained in the aforesaid cornmeal broth at a temperature between 24°-30° C. for three days at which time the contents of the Fernbach flask were transferred into a 30 liters fermentation tank containing an aqueous growth media and maintained at a temperature between 24°-30° C. for three days. The contents of the 30 liters fermentation tank were then transferred into a 240 liters fermentation tank containing an identical aqueous growth media and permitted to remain therein at a temperature between 24°-30° C. for three days. The mass within the 240 liters tank was then transferred to a 2000 liters tank and caused to incubate at a temperature between 24°-30° C. for about five days.

The aqueous growth media in each of the fermentation tanks contained the following ingredients in the concentrations indicated:

|  | grams/liter |
| --- | --- |
| potassium diphosphate | 0.25 |
| potassium monophosphate | 0.10 |
| yeast extract | 0.75 |
| glucose | 6.00 |
| sodium chloride | 0.10 |
| magnesium sulphate | 0.10 |

Similarly, a strain of Rhizobium bacterium maintained on an agar slope may be started by first washing the slope with 10 ml. of an aqueous growth media and capturing the wash liquid in a test tube. The contents of the test tube are initially incubated at a temperature between 24°–30°C. for three days. The test tube culture is then transferred successively and at three day intervals first into 150 ml., then into 300 ml., then into 1500 ml., then into 30 liters and then into 240 liters of an aqueous growth media. Finally, the 240 liters mass is transferred into a 2000 liters incubation tank where it is grown to maturity in five days.

The aqueous growth media used to grow the Rhizobium bacterium in each of the transfer vessels is the same as is used to grow the Arthrobotrys fungus, except for the addition of 0.001 gram per liter of sodium molybdate and 0.005 gram per liter of ferrous sulphate to the Rhizobium growth media.

At maturity, the contents of the 2000 liters incubation tank containing the mature Rhizobium culture may be centrifuged to separate and recover a concentrated, paste-like mass containing upwards of $6 \times 10^{11}$ cells (CFU) of Rhizobium bacterium per gram. This paste-like mass of Rhizobium cells may then be frozen to a temperature between $-15°$ and $-30°$ C. to place the Rhizobium bacterium in a substantially dormant (not reproducing) condition.

The mature Arthrobotrys fungal culture and the frozen Rhizobium bacterial culture, as previously described, are combined with one or more carbohydrate nutrients to prepare legume-inoculating compositions according to this invention. The legume-inoculating compositions of this invention preferably take the form of frozen liquid concentrates which may be thawed and diluted with water prior to their introduction into the soil. However, the present composition may also be prepared and sold in the form of a dry powder which is used to dust and coat legume seeds prior to their planting, or in the form of a granular bulk material which can be incorporated in the soil during preparation of the seed bed prior to planting, or deposited in the furrow at planting.

Regardless of the particular physical forms in which the present compositions are prepared and distributed for use, they must include at least one viable propagule of the selected Arthrobotrys fungus and at least one million cells (CFU) of the selected Rhizobium bacterium per gram of the composition introduced into the soil, together with a sufficient quantity of carbohydrate nutrient to sustain growth of the fungus and bacterium for a reasonable period of time following their introduction into the soil. Preferably, the present compositions are formulated to supply between $1 \times 10^5$ and $1 \times 10^6$ propagules of Arthrobotrys fungus and between $1 \times 10^6$ and $1 \times 10^9$ cells (CFU) of Rhizobium bacterium per gram of composition as it is introduced into the soil.

As a specific example of the preparation of a composition according to this invention, 24 kilograms of a frozen Rhizobium japonicum culture having a cell count of approximately $6 \times 10^{11}$ CFU per gram were thawed and mixed by mechanical stirring and air injection with the contents of a 2000 liter incubation tank containing a mature Arthrobotrys amerospora culture having a growth concentration of approximately $1 \times 10^6$ propagules per gram. To this mixture was added 182 liters of glycerol and 18 kilograms of glucose (Cerelose hydrate). Following a complete blending of the foregoing ingredients, the liquid mixture was divided into equal volume aliquots which were placed into semi-flexible polyethylene bottles and frozen and maintained at a temperature between $-15°$ and $-30°$ C.

A dry, seed-coating composition suitable for the preplant dusting and coating of legume seeds may also be prepared by combining the following ingredients in a horizontal ribbon mixer:

|  | (% by wt.) |
| --- | --- |
| a viable liquid culture containing from $7 \times 10^6$ to $7 \times 10^9$ propagules Arthrobotrys fungi and from $1 \times 10^{14}$ to $2 \times 10^{15}$ CFU of Rhizobia bacteria in water with trace minerals | 23.05 |
| dry montmorilonite clay | 50.80 |
| dry sodium bentonite clay | 25.40 |
| dry cornmeal | 0.75 |

Following complete blending, this mixture is then air dried to a total moisture content of approximately 5% by weight to thereby place the biological mixture in a dormant (nonreproducing) state.

A dry granular composition suitable for direct incorporation in the soil may be prepared by mixing 1 part by weight of the previously described dry, seed-coating composition with 6 parts by weight of sodium bentonite clay, ground corn cobs, or mixtures of each.

Another form of granular composition according to this invention, and suitable for direct application into the soil, may be prepared simply by substituting equal weights of ground, granular peat and glucose (Cerelose hydrate), respectively, for the clays and cornmeal constituents of the previously described seed-coating composition.

Test Results

In-field tests and experiments have been conducted to evaluate the efficacy of the present legume-inoculating composition in the production of peanuts, green bush beans and soybeans at three different farms located near Leesburg, Ga., Homestead, Fla. and Sanford, Fla., respectively.

In these experiments, the present composition was tested in the same fields and under as nearly equal conditions as possible against adjacent untreated control areas and against adjacent areas treated only with a Rhizobium bacterium specific to the legume inoculated. The purpose of these tests was to determine the effects of the present composition on plant growth, root nodulation, crop yield, root-knot galling and foliage coloration in comparison with untreated control plants and plants inoculated only with Rhizobium bacteria. Each of these tests revealed that the plants which were inoculated with the present Arthrobotrys-Rhizobium composition were significantly improved in every respect as compared with the untreated control plants and with plants inoculated with Rhizobia bacteria only.

In a particular experiment conducted at the Institute of Food and Agriculture Science substation near Sanford, Fla. during the months of July through December 1981, approximately 2 acres of ground which had been pretreated with a granular nematocide (Nemacur) at an application rate of 26.7 pounds per acre was selected as a test area. The entire test area was prepared into a good seed bed for the planting of soybeans and four test plots of approximately equal areas were laid out for four replicate tests using randomly assigned rows. Each test plot included a control group consisting of rows of untreated soybeans, a first treatment group consisting of soybeans inoculated in the furrow at the time of planting with *Rhizobium japonicum* applied at a rate of $8.94 \times 10^4$ CFU/cm., a second treatment group consisting of soybeans inoculated in the furrow at the time of planting with a composition according to this invention which included *Arthrobotrys amerospora* and *Rhizobium japonicum* and a nutrient and which was applied at a rate of 220 ml. of the frozen liquid concentrate per acre ($2.19 \times 10^5$ CFU of *Rhizobium japonicum* per cm. of furrow).

The soybean plants grown in each of the four test plots were periodically observed from time of sprouting to harvest and samples were taken and measured at their bloom stage of growth and at harvest. The following table is a summary of the results of these observations and the data shown represents an average of the four test plots. In the following table, the letter (A) designates the untreated control plants, the letter (B) designates plants inoculated with *Rhizobium japonicum* only and the letter (C) designates plants inoculated with a combination of *Arthrobotrys amerospora*, *Rhizobium japonicum* and nutrient according to the present invention.

peanuts. In this test, a six acre field was plowed, disced and worked up into a good firm seed bed preparatory to planting. A first two acre plot in the field was treated, concurrently with discing and prior to planting, by incorporating into the soil a tap water-diluted solution containing 16 oz. of the present *Arthrobotrys amerospora*-Rhizobium spp.-nutrient composition. A second two acre plot was treated at the time of planting and by dripping into the seed furrows a tap water-diluted solution containing 4 oz. of the present *Arthrobotrys amerospora*-Rhizobium spp.-nutrient composition. A third two acre plot, designated as a control plot, was treated at the time of planting by incorporating into the seed furrows a peat granular form of Rhizobium spp. at a rate of 6 oz. per 1000 linear feet of furrow (approx. $1.44 \times 10^5$ CFU/cm.). All three plots were planted on the same day and all plots were harvested in one day approximately six months after planting. These plots were observed periodically throughout the growing season and the plants inoculated with the present Arthrobotrys-Rhizobium inoculum were notably darker in foliage color than the plants inoculated with Rhizobium spp. only.

Ten growing plant samples were taken from each of the two acre plots just prior to bloom and again following bloom and pegging and the root nodules were counted and averaged and the roots were checked for nematodes. The plants were harvested and average yields were determined on the basis of plants taken from 0.25 acre in each two acre plot.

| | SUMMARY OF TESTS | | | |
|---|---|---|---|---|
| PLANTS | NODULE COUNT (before bloom) | NODULE COUNT (after bloom) | ROOT-KNOT NEMATODES OBSERVED | YIELD (lb./acre) |
| AL-1 | 134 | 142 | yes | 5,640 |
| AL-2 | 292 | 297 | no | 6,780 |
| AL-3 | 318 | 321 | no | 6,800 |

AL-1 = plants inoculated in the furrow with Rhizobium spp. only.
AL-2 = plants inoculated by preplant incorporation of *Arthrobotrys amerospora* combined with Rhizobium spp.
AL-3 = plants inoculated in the furrow with *Arthrobotrys amerospora* combined with Rhizobium spp.

A further test was conducted during the months of November 1981 through January 1982 at a farm near Homestead, Fla. to determine the comparative efficacy

| | SUMMARY OF TEST DATA | | | | | |
|---|---|---|---|---|---|---|
| PLANTS | FOLIAGE COLOR* | PLANT HEIGHT (cm.) | 10 PLANTS DRY WT. (g.) | NO. OF NODULES | YIELD Bu/Ac. | ROOT-KNOT GALLING* |
| A | 4.2 | 66.4 | 51.4 | 15.2 | 11.8 | 4.8 |
| B | 8.5 | 81.3 | 109.0 | 127.2 | 27.5 | 4.5 |
| C | 10.0 | 92.1 | 117.6 | 353.8 | 37.8 | 0.2 |

*Foliage color: (scale 0–10) with 0 = yellow green and 10 = dark green.
**Root knot galling index: (scale 0–10) with 0 = no galling and 10 = severe galling.

As will be noted, the soybean plants (C) which had been inoculated with the present Arthrobotrys-Rhizobium inoculum showed significant improvements in foliage color, plant growth, nodulation, yield and root-knot galling as compared with the untreated (control) plants (A) and with the plants (B) which had been inoculated with *Rhizobium japonicum* only. The yield of plants (C) was 137% greater than plants (B) and 318% greater than plants (A).

As used hereinafter, Rhizobium spp. refers to a species of Rhizobium specific to peanuts.

Another experimental test was conducted during the months of May through October 1981 on a farm near Leesburg, Ga. to evaluate the efficacy of the present Arthrobotrys-Rhizobium inoculum in the production of of the present Arthrobotrys-Rhizobium-Nutrient composition in comparison with a *Rhizobium phaseolus* inoculum only. In this test, a good firm seed bed was prepared by discing and tilling the soil to desired texture and fertilizing with ammonium nitrate at the rate of 40 lb./acre.

One acre of the prepared field was designated as a control plot and was treated at the time of planting by dripping a tap water-diluted solution of a *Rhizobium phaseolus* concentrate (LEGUME-AID frozen concentrate) into the seed furrows at a rate of $1 \times 10^6$ CFU/cm. prior to closure of the furrows. Another one acre plot in the field was treated at the time of planting by dripping a tap water-diluted solution of the present *Arthrobotrys amerospora-Rhizobium phaseolus*-nutrient composition into the seed furrows at the same rate of $1\times 10^6$ CFU/cm.

The plants in each of these one acre plots were observed periodically throughout the growing season and it was noted that the plants treated with the present composition were taller by an average of about 2 inches and were 3 indices darker in foliage color than the control plants which had been treated with the *Rhizobium phaseolus* only. At harvest, the yield of the plants treated with the present composition was 109 pounds per acre greater than the yield of the control plants.

The results of these and various other tests and experiments indicate that the effect of the present composition is synergistic and may possibly be attributed to a symbiotic relationship between the Arthrobotrys fungi and the Rhizobia bacteria and the inoculated plant.

In view of the foregoing, it will be seen that this invention provides a stable, easily applied legume-inoculating composition whose use results in unusual and unexpected improvements in plant growth and crop yield.

We claim:

1. A legume-inoculating composition comprising, as essential ingredients:
   (a) a viable fungus of the genus Arthrobotrys,
   (b) a bacterium of the genus Rhizobium, and
   (c) a nutrient for said fungus and said bacterium selected from the class consisting of a monosaccharide, a disaccharide, a polysaccharide, glycerol and cornmeal; the Arthrobotrys fungus being present in an amount equal to at least one propagule per gram of said composition and the Rhizobium bacterium being present in an amount equal to at least one million cells per gram of said composition.

2. A composition according to claim 1, wherein the amount of Arthrobotrys fungus present in said composition ranges from one hundred thousand to one million propagules per gram of said composition, the amount of Rhizobium bacterium present in said composition ranges from one million to six billion cells per gram of said composition, and the amount of nutrient present in said composition ranges from 0.001 to 0.1 gram per gram of said composition.

3. A composition according to claim 1, wherein said fungus is of the species *Arthrobotrys amerospora*.

4. A composition according to claim 1, wherein said bacterium is a species of Rhizobium specific to the species of legume to be inoculated.

5. A composition according to claim 1, wherein said fungus is of the species *Arthrobotrys amerospora* and said bacterium is a species of Rhizobium specific to the species of legume to be inoculated.

6. A composition according to claim 1, wherein said composition is in a non-reproductive, frozen liquid state.

* * * * *